United States Patent
Riemer et al.

(10) Patent No.: US 9,089,378 B2
(45) Date of Patent: Jul. 28, 2015

(54) KIRSCHNER WIRE CLAMP

(75) Inventors: Rose Riemer, Solothurn (CH); Roland Kebel, Solothurn (CH); Roger Tanner, Niederwangen (CH)

(73) Assignee: Stryker Trauma GmbH (DE)

( * ) Notice: Subject to any disclaimer, the term of this patent is extended or adjusted under 35 U.S.C. 154(b) by 1134 days.

(21) Appl. No.: 12/321,378

(22) Filed: Jan. 16, 2009

(65) Prior Publication Data
US 2010/0211078 A9    Aug. 19, 2010

(30) Foreign Application Priority Data

Jan. 22, 2008   (DE) ............... 20 2008 000 914 U

(51) Int. Cl.
*A61B 17/56*   (2006.01)
*A61B 17/58*   (2006.01)
*A61B 17/88*   (2006.01)
*A61B 17/84*   (2006.01)
A61B 17/80    (2006.01)

(52) U.S. Cl.
CPC ........... *A61B 17/8861* (2013.01); *A61B 17/842* (2013.01); *A61B 17/8047* (2013.01); *A61B 17/848* (2013.01); *A61B 17/8872* (2013.01)

(58) Field of Classification Search
CPC .................... A61B 17/8861; A61B 17/848
USPC .......... 606/103, 104, 105, 324, 329; 292/303, 292/353; 24/129 R, 129 B, 910; 403/109.3, 403/224; 248/316.7
See application file for complete search history.

(56) References Cited

U.S. PATENT DOCUMENTS

| | | | | |
|---|---|---|---|---|
| 185,127 A | * | 12/1876 | Peck | 24/703.4 |
| 977,704 A | * | 12/1910 | Brownlee | 52/686 |
| 2,216,886 A | * | 10/1940 | Langelier | 248/311.2 |
| 2,279,068 A | * | 4/1942 | Siebrandt | 140/121 |
| 2,654,932 A | * | 10/1953 | Goudie | 24/523 |
| 3,295,812 A | * | 1/1967 | Schneider et al. | 248/229.16 |
| 3,415,473 A | * | 12/1968 | Ollen | 248/59 |
| 4,036,460 A | * | 7/1977 | Storck et al. | 248/59 |
| 4,920,958 A | * | 5/1990 | Walt et al. | 606/96 |
| 6,077,268 A | | 6/2000 | Farris et al. | |
| 7,192,432 B2 | * | 3/2007 | Wetzler et al. | 606/96 |
| 7,232,443 B2 | | 6/2007 | Zander et al. | |
| 2005/0173949 A1 | * | 8/2005 | Hart | 297/171 |
| 2006/0195104 A1 | | 8/2006 | Schlafli et al. | |
| 2007/0225716 A1 | * | 9/2007 | Deffenbaugh et al. | 606/69 |

FOREIGN PATENT DOCUMENTS

| | | |
|---|---|---|
| AT | 353559 T | 3/2007 |
| CA | 2405235 A1 | 2/2001 |

(Continued)

*Primary Examiner* — Matthew Lawson
*Assistant Examiner* — Zade Coley
(74) *Attorney, Agent, or Firm* — Lerner, David, Littenberg, Krumholz & Mentlik, LLP

(57) ABSTRACT

A Kirschner wire clamp is used to reliably and simply fix bone plates to a bone surface. The wire clamp consists of a tubular guide member for receiving a Kirschner wire. The guide member has a bore surrounded by a wall and a base for engaging a hole in a bone plate such as a bone screw hole. A spring clamp is mounted adjacent an open end of the tubular guide bore opposite the base which clamps the Kirschner wire to the guide member after the wire has been fixed in bone. The Kirschner wire clamp can be aligned simply and reliably by the guide member, and by the clamping mechanism, can be reliably fixed to the Kirschner wire.

7 Claims, 4 Drawing Sheets

(56) References Cited

FOREIGN PATENT DOCUMENTS

| DE | 75194 A | 3/1969 |
| DE | 29913994 U1 | 12/2000 |
| DE | 102004014036 A1 | 10/2005 |
| FR | 1161507 A | 9/1958 |
| WO | 2007075791 A2 | 7/2007 |

* cited by examiner

KIRSCHNER WIRE CLAMP

CROSS-REFERENCE TO RELATED APPLICATIONS

This application claims the benefit of the filing date of German Utility Model Application No. 20 2008 000 914.6 filed Jan. 22, 2008.

BACKGROUND OF THE INVENTION

The present invention relates to a Kirschner wire clamp for positioning a bone plate, in particular a Kirschner wire clamp, which allows more precise, easier and simpler positioning of a bone plate on a bone surface.

In the treatment of bone fractures it is helpful and sometimes necessary that, prior to fixation of a fracture by bone plates, the fracture itself is stabilized. This is, in particular, helpful or necessary in cases where the bone fracture not only comprises two fragments but a multitude of fragments. In this case it may be necessary to stabilize the multitude of fragments in their original position before fastening corresponding bone plates and bone screws for fixation of the fracture. Such stabilization and preliminary fixation are often achieved by so-called Kirschner wires, whose tips comprise a cutter that makes it possible, by a corresponding drill, to drill the Kirschner wires into and through the bone or the bone fragments and in this way to stabilize the bone fragments relative to each other. However, these Kirschner wires may be inadequate for fixation until final healing, so that subsequent positioning of bone plates needs to take place. In this process, Kirschner wires can be used to support positioning of a bone plate to be put in place. For this purpose, for example, a bone plate is placed on the corresponding bone surface, and a Kirschner wire is placed through a hole in the bone plate. A Kirschner wire clamp is placed on a Kirschner wire anchored in the bone. The bone plate can be placed on the bone or on the bone surface, and can also be fastened to the wire, such that the corresponding bone screws can be fixed simply and reliably through the remaining free openings or through-holes in the bone plate. By temporary attachment of the plate, additional hands (operating theatre personnel) can be saved, and, in order to check whether the fracture has been restored properly, the bone can be moved and rotated without the plate falling off, in particular if the plate is in an upside-down position as a result of rotation of the bone.

However, the Kirschner wire clamps known from prior art are difficult to handle, making it hard to carry out satisfactory preliminary fixation of a bone plate, comprise only limited functionality, or require significantly more time and space for their use.

BRIEF SUMMARY OF THE INVENTION

The subject matter of the present application provides for a Kirschner wire clamp that makes fast and easy positioning possible.

According to an exemplary embodiment of the invention, a Kirschner wire clamp is provided with a guide element, a base element and a clamping element, wherein the base element is arranged at a first end region of the guide element, wherein the clamping element comprises a clamping region, wherein the clamping region is arranged in a longitudinal direction of the guide element above, or spaced apart from, a second end region of the guide element.

In this way a situation can be achieved in which the alignment of the base element takes place by the guide element on the Kirschner wire that has been put in place, so that, for example, a bone plate can be fixed to a bone surface by the base element. This makes it possible, in particular, to exactly align and reliably and quickly fix the bone plate by the Kirschner wire positioned in the bone. In this application the term guide element refers to an arrangement that makes it possible to align the Kirschner wire clamp on a Kirschner wire that has been put in position. However, the guide element can also be used to significantly simplify the narrow access to the bone or the plate through the soft tissue, and to ensure that the more space-intensive clamping element is situated outside the soft tissue. In this case the guide element can be used to guide the Kirschner wire through the tissue. In this arrangement a base element can be used as a foundation for defined fixing, and as a contact pressure element on the bone plate. The base element can be designed as a separate element, but it can equally be integrated in the end region of the guide element. In this arrangement the guide element and the base element can be designed in one piece; in other words the base element can make a gradual transition to the guide element. However, the base element can also be joined to the guide element such as being threaded thereon. The base element can also be spaced apart from the first end region by spacers, wherein in this case the spacers are considered to form part of the base element. The term "clamping element" refers to an element that is able to fix the Kirschner wire on the Kirschner wire clamp in a frictionally engaged manner or having positive fit so that the position of the Kirschner wire clamp relative to the Kirschner wire can essentially no longer be changed just like that, i.e. without further exertion of force or without renewed operation of the clamp. In this context the term "above" refers to a continuation of the axis or line of longitudinal extension of the guide element in the direction of the second end region (away from the bone), and in this context can also be in direct contact with the second end region.

According to an exemplary embodiment of the invention, the base element comprises a fitting region, wherein the fitting region is designed to engage a through-hole of a bone plate.

The base element, which is, for example, fixed as an end region of the guide element, can thus comprise a fitting region at the position at which the Kirschner wire clamp presses against the bone plate to be fixed. In this arrangement it is possible, by the fitting region, for example to bring about positioning or centering of the base element on or in the through hole of a bone plate. In this arrangement the fitting region can have various embodiments, and can, for example, be designed to match through-openings or through-holes of bone plates. Of course, it is also possible for through-openings of bone plates to be designed so as to match the corresponding fitting regions of a Kirschner wire clamp, so that reliable fixing of the bone plate to the bone surface can take place. In this arrangement the through-holes can be designed with or without threads. In cases where the diameter of a Kirschner wire is essentially the same as that of a through-hole of a bone plate, the positive-fit connection between a face of the Kirschner wire clamp, which face points towards the plate, and the plate surface that surrounds the through-hole is established.

According to an exemplary embodiment of the invention, the fitting region comprises a through-hole, wherein the through-hole extends in a direction that essentially corresponds to an axis of longitudinal extension of the guide element.

In this manner it is possible to fix the bone plate by guiding the Kirschner wire through the fitting region or by the base element, which makes possible precise alignment of the Kirschner wire clamp and thus precise positioning of the bone plate on the bone surface.

According to an exemplary embodiment of the invention, the fitting region tapers off in one direction, wherein this direction corresponds to a direction of longitudinal extension of the guide element and points away from said guide element.

In this way it may become possible, by the base element which for example tapers off in the direction of the bone plate, or by the fitting region, to achieve automatic centering of the Kirschner wire in the through-hole of the bone plate. Furthermore, displacement of the bone plate may be prevented in this manner so that more reliable fixing of the bone plate to the bone surface is made possible.

According to an exemplary embodiment of the invention, the guide element is designed to accommodate a Kirschner wire that has been put in place in a bone and that protrudes from the bone and through a through-hole of a bone plate.

In this manner reliable fixing relating to the contact pressure and the position is made possible by the guide element accommodating the Kirschner wire. In this arrangement the through-hole of a bone plate can be a hole that is intended for accommodating a screw; but it can also be a special hole that is intended for guiding a Kirschner wire through it.

According to an exemplary embodiment of the invention, the guide element is designed so as to be straight and tubular in shape.

A straight design of the guide element makes it possible to insert a Kirschner wire, which as a rule is also straight, without any problems, wherein the tubular design prevents the Kirschner wire from unintentionally slipping from the guide element, which would make positioning of the bone plate on the bone surface more difficult. However, a curved sleeve is also possible, in which the Kirschner wire is clamped by the curvature so as to be fixed. In this arrangement the sleeve can be designed so as to be elastic so that by a further tool, for example suitable pliers it can be brought to straight alignment for the purpose of moving the Kirschner wire in or out. In this case an end region, arranged at a distance from the base element, of such a sleeve, which is also used as a guide element, will have to be considered as being the clamping region, wherein the actual guide element then extends from an end region, which faces the base element, to the interior wall region of the sleeve, which interior wall region is located radially opposite the clamping region in the sleeve, and is used as an abutment for clamping the Kirschner wire.

According to an exemplary embodiment of the invention, the clamping element comprises a leaf spring or an elastic region, such as a bent region, that is used as a leaf spring.

A leaf spring has a simple geometric shape that is easy to clean, by which a clamping region of the clamping element can clamp-fix the Kirschner wire to the Kirschner wire clamp.

According to an exemplary embodiment of the invention, the clamping element is movable between a first position and a second position, wherein the clamping region is designed in the first position to laterally press a Kirschner wire that protrudes beyond the second end region to an interior wall region of the guide element.

In this arrangement the clamping element can fix the Kirschner wire to the guide element not only in a frictionally engaged manner and/or having positive fit on the inside of the guide element, but the clamping element can also fix the Kirschner wire to the clamping region itself in a frictionally engaged manner and/or having positive fit. In this arrangement the clamping region can produce a frictionally engaged connection with the Kirschner wire, however, additionally or as an alternative, it can also establish a positive-fit connection by minimum deformation of the Kirschner wire in the clamping region, which connection prevents the Kirschner wire clamp from sliding from the Kirschner wire. In this manner reliable fixing of the Kirschner wire clamp to the Kirschner wire, and thus reliable fixing of the bone plate to the bone surface, is made possible.

According to an exemplary embodiment of the invention, the clamping element comprises a recess or a hole as a clamping region, wherein the clamping element further comprises a fastening region that is attached to the guide element.

In this arrangement a hole in the clamping element may prevent the Kirschner wire from unintentionally moving or sliding from its normal position, whereas a recess with, for example, a lateral opening makes it possible to insert the Kirschner wire also laterally into the clamping element, for example if this is required for reasons of available space. In this arrangement the clamping element can comprise a cutting edge that improves fixing the Kirschner wire to the contact position of the clamping region. The fastening region of the clamping element can be attached to the guide element, for example by soldering, adhesively bonding, welding and in particular laser welding, or by a press fit.

According to an exemplary embodiment of the invention, the recess or the hole in the second position corresponds with the direction of longitudinal extension of the guide element such that a Kirschner wire that protrudes beyond a bone and through a through-hole of a bone plate can be inserted into the guide element in a direction of longitudinal extension of the guide element.

In other words the clamping element that is in the second position makes it possible to position the Kirschner wire clamp on the Kirschner wire, wherein fixing the Kirschner wire clamp on the Kirschner wire takes place by a movement of the clamping element to the first position. It should be mentioned that the clamping element can take still further positions, wherein in particular the home position of the clamping element can be a position that differs from the first position and the second position. In particular, in this arrangement the first position can be located between the second position and the home position. Furthermore, it should be mentioned that the clamping element can be moved from the home position to the first position or to the second position by exertion of force in which the leaf spring is moved out of its home position.

According to an exemplary embodiment of the invention, the clamping element comprises the following regions along its extension in the following order: a first gripping region, a fastening region, an elastic region, a clamping region and a second gripping region.

As a result of the gripping regions it is possible for an operator to move the clamping element between the different positions in that the clamping element is subjected to deformation, in particular to reversible deformation, in the elastic region, e.g. in a leaf spring region. In this arrangement the clamping element can be deflected in order to make single-handed operation possible. As a result of the arrangement of an attachment region, an elastic region and a clamping region between the first gripping region and the second gripping region, the lever arms of the clamping element can be selected to be large so that activation, in particular deformation of the elastic region, can be carried out simply by single-handed activation. Furthermore, as a result of such a design the clamping region can be moved precisely and easily so that simple and precise operation of the Kirschner wire clamp becomes possible.

According to an exemplary embodiment of the invention, the clamping element, the guide element and the base element are open towards one side such that a Kirschner wire that protrudes beyond a bone and through a through-hole of a bone plate can be inserted laterally into the guide element.

In this arrangement, for example, a hole present in the clamping element can comprise a lateral opening so that the Kirschner wire can be laterally inserted to the hole located in the clamping element without "threading" having to take place by way of the end of the Kirschner wire. Likewise, the attachment region of the clamping element can be laterally open in the region of the guide element in order to make it possible to laterally insert a Kirschner wire. Such a lateral opening is in particular advantageous if the available space is restricted or if the end of the Kirschner wire is not easily accessible just like that, or if, due to the inherent situation of an operation the Kirschner wire clamp cannot be moved to the bone plate by way of the free end of the Kirschner wire with its base element.

According to an exemplary embodiment of the invention, in defined regions the clamping element can be designed so as to laterally taper off, in particular in the elastic region of the clamping element, in order to in this way make possible easier deformability or elastic bendability of the clamping element.

It should be noted that the individual features can of course also be combined, as a result of which, in part, advantageous effects may arise which exceed the sum of the individual effects.

These and other aspects of the present invention are explained and clarified with reference to the exemplary embodiments described hereafter.

BRIEF DESCRIPTION OF THE DRAWINGS

Below, exemplary embodiments are described with reference to the following drawings.

DETAILED DESCRIPTION

Figure 1:
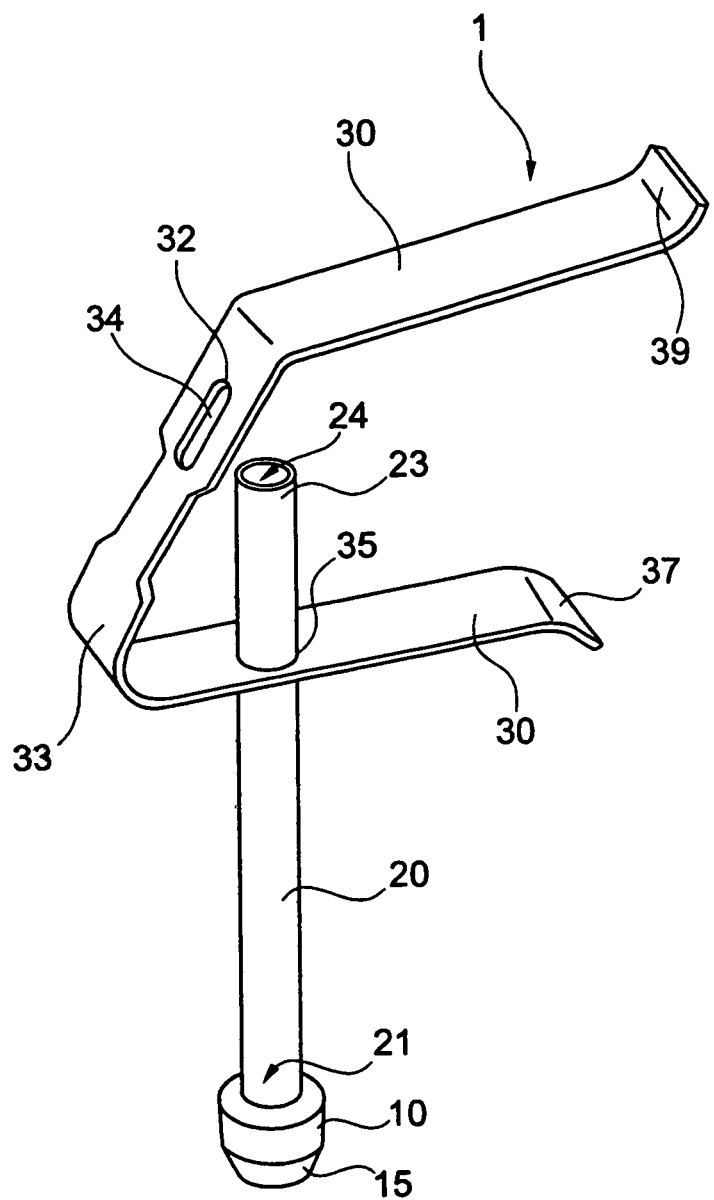
FIG. 1 shows a perspective view of a Kirschner wire clamp according to the invention.
Figures 2, 2A:
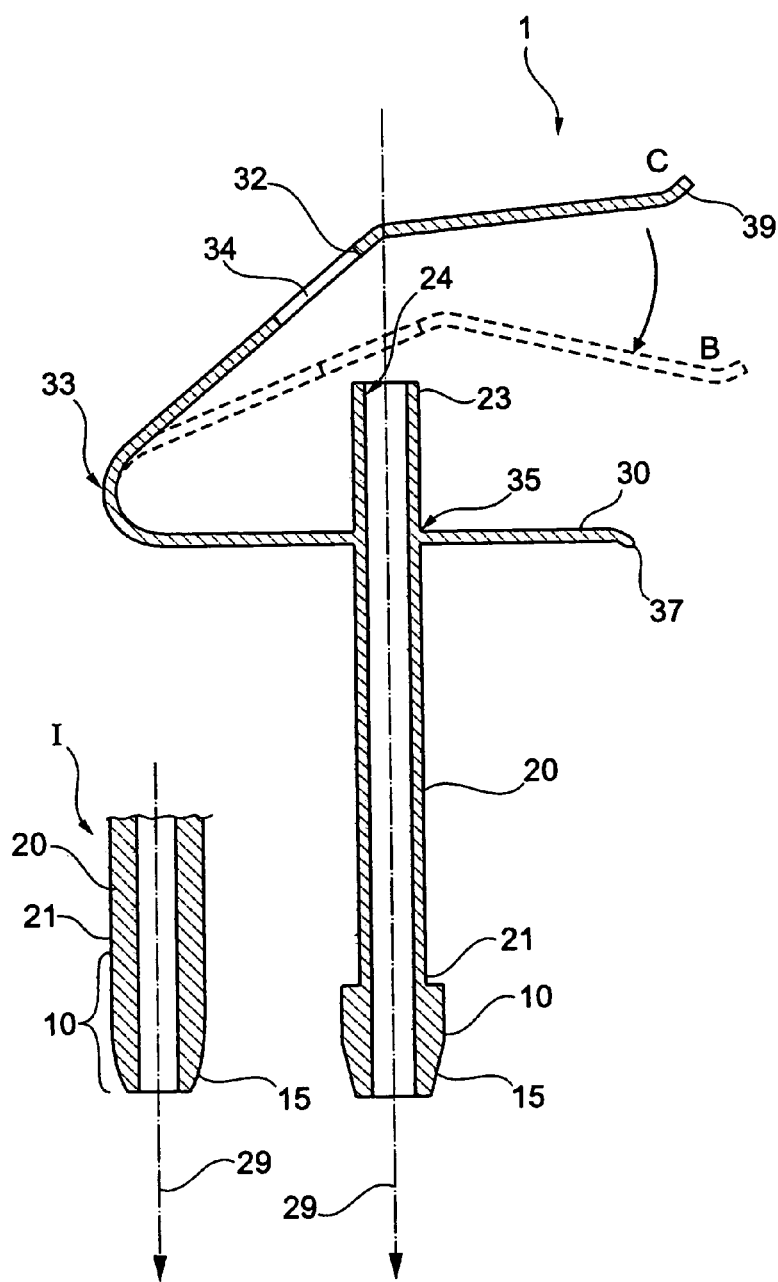
FIG. 2 shows a section view of a Kirschner wire clamp according to the invention with two possible positions of the clamping element.
FIG. 2A is an enlarged view of an end region of an alternate Kirschner wire clamp.
Figure 3:
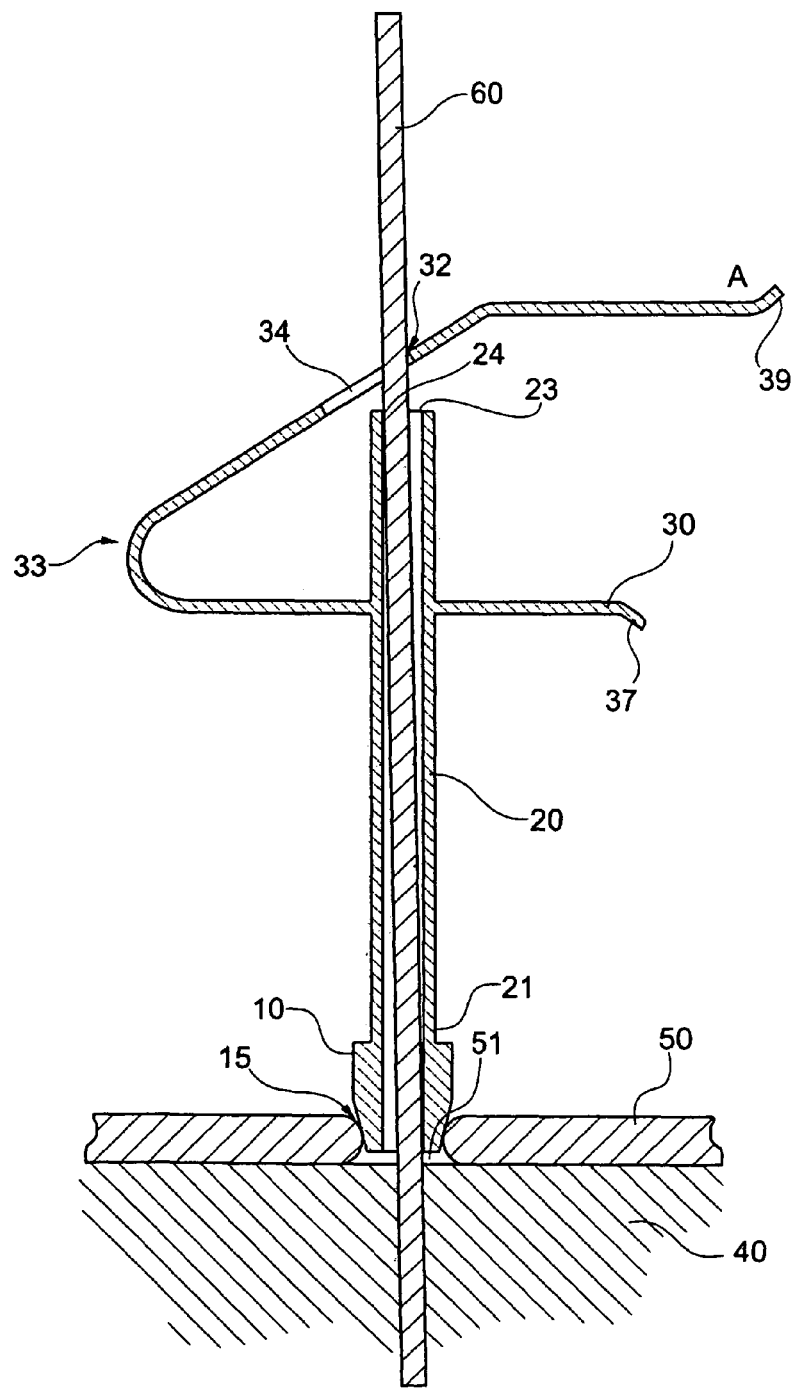
FIG. 3 shows a Kirschner wire clamp according to the invention in an installed state together with a fixed Kirschner wire and a bone plate located on a bone surface.

Referring to FIG. 1 there is shown a perspective view of a preferred Kirschner wire clamp 1 according to the invention. The Kirschner wire clamp 1 shown in FIG. 1 comprises a guide element 20. Furthermore, a base element 10 is provided, which is located in a first end region 21 of the guide element 20. In the preferred embodiment shown, the base element 10 comprises a diameter that exceeds that of the guide element. However, this is not mandatory. Instead, the base element can also be formed to the guide element so as to make a gradual transition, as shown in FIG. 2A in the tip section designated I. In this case that part which essentially is used to guide a Kirschner wire is to be understood to be the guide element, while the base element is understood to be the part which essentially is used as a foundation for the Kirschner wire clamp on the bone plate 50 as shown in FIG. 3. The exertion of force for fixing the bone plate 50 takes place by way of base element 10. In the embodiment shown the base element comprises a fitting region 15, which in the embodiment shown tapers off in the direction pointing away from the guide element. This fitting region makes it possible to fit the base element into a through-opening 51 of a bone plate 50, wherein tapering off is used for positioning or centering base element 10 in through-hole 51 of bone plate 50. Base element 10 applies a clamping force around the circumference of screw hole 51 in plate 50 as shown in FIG. 3.

Figure 4:
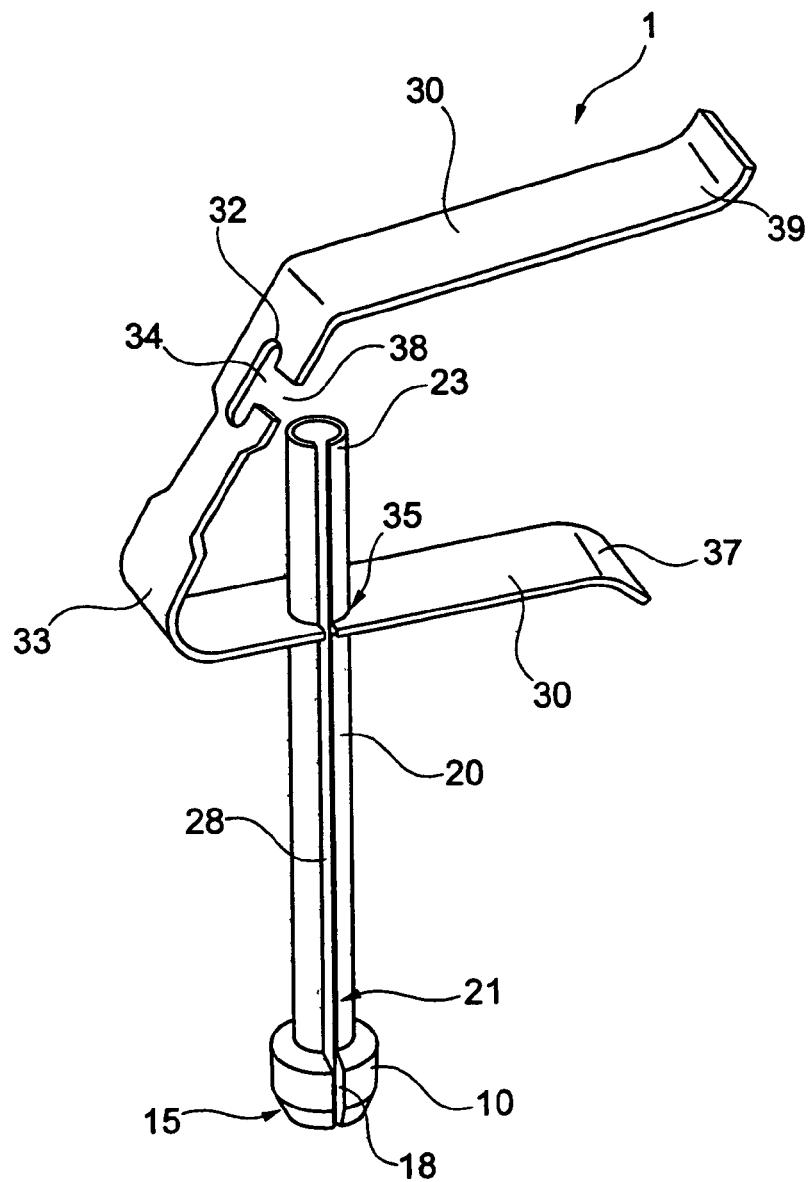
FIG. 4 shows a Kirschner wire clamp according to a further exemplary embodiment with a lateral opening.

The Kirschner wire clamp comprises a clamping element 30 that is attached in an attachment region 35, for example by adhesive bonding, a solder connection, a weld connection and in particular a laser weld connection, by a press fit or even integrally formed therewith. The clamping element 30 further comprises a clamping region 32 that is situated above the second end region 23 of the guide element 20. In this context the term "above" refers to the clamping region being located in the direction of the opening of the guide element 20 in the region of the second end region 23, without mandatorily being located in each position above the opening of the second end region 23. In some excursion positions clamping region 32 can also be situated beside the longitudinal axis of the guide element 20. In this arrangement the clamping region 32 can be situated in an opening, a recess 38 as shown in FIG. 4 or a through-hole 34 of clamping element 30, wherein the through-hole can be a round hole or an elongated hole, or a hole with any desired cross-sectional shape. In at least one region clamping element 30 comprises an elastic section 33 through which the two limbs of clamping element 30 can be moved by the gripping regions 37, 39. Elastic section 33 can be a bent region about which gripping arms 37, 39 are deflected. The guide element 20 further comprises an interior wall region 24 against which, in the region of the second end region 23, a Kirschner wire can be pushed through the clamping region 32 of the clamping element 30 in order to in this way fix the Kirschner wire to the Kirschner wire clamp. In this arrangement gripping regions 37, 39 can, for example, comprise a certain curvature in order to prevent slipping during manual operation. In this arrangement all the edges including gripping regions 37, 39 can be designed such that, for example, they cannot damage the protective gloves of an operator.

The Kirschner wire clamp can essentially be made from surgical steels, wherein the materials used can be suitably selected by an average person skilled in the art as far as their sterilizability, stability or deformability are concerned. Transitions, for example in the fastening region 35 or between guide element 20 and base element 10, can be designed such that any depositing of particles can be prevented, for example by a design with gradual transitions.

Of course, the Kirschner wire clamp can also, entirely or in part, be made of other suitable materials, for example plastics or fibre-reinforced materials, provided they are suitable for application as a Kirschner wire clamp. This may be advantageous, in particular, in the case of single-use as a disposable Kirschner wire clamp, due to low production costs.

Referring to FIG. 2 there is shown a section view of an exemplary embodiment of a Kirschner wire clamp according to the invention. In the section view shown, at least a region of clamping element 30 can be brought from the home or relaxed undeflected position C to a second position B by deformation of the elastic region 33 so that the opening 34 corresponds to the opening in the bore of the guide element 20 in the second end region 23. In this excursion state a Kirschner wire can be fed through the guide element 20 and the aperture 34, wherein the Kirschner wire with clamping region 32 can be clamped to an interior wall side 24 in the end region 23 of guide element 20. In this arrangement clamping can take place either in the wall region 24 or in the clamping region 32. In this context the term "clamping region" 32 only refers to the fact that clamping of the Kirschner wire takes place, wherein it is not mandatory for the frictionally engaged fit or positive-fit connection to take place in clamping region 32 but instead it can also take place at the interior wall region 24. However, for improved insertability of the Kirschner wire, the interior of guide element 20 can also comprise an adhesion-reducing coating so that in this case it may be sensible to establish the frictionally engaged fit between the Kirschner wire and the clamping region 32 in order to cause reliable fixing of the Kirschner wire clamp 1 to the Kirschner wire.

In this arrangement elastic region 33 need not be limited to the position designated in FIG. 2, but instead can also extend across larger regions or across the entire clamping element 30.

Referring to FIG. 3 there is shown a Kirschner wire clamp according to the invention in a position A that fixes a bone plate 50 to a bone 40. In this arrangement a Kirschner wire 60 extends from bone 40 through a through-opening or a through-hole 51 of bone plate 50. In this arrangement the Kirschner wire clamp is pushed over the Kirschner wire 60 into a location that in FIG. 2 is designated position B, wherein the clamping element, which during installation is subjected to an excursion movement to position B, is subsequently released so that it moves to position A. Due to the inserted Kirschner wire 60 clamping element 30 cannot return to its original home position C (FIG. 2) but instead with the clamping region 32 presses the Kirschner wire 60 to the interior wall region 24 of the second end region 23 of guide element 20. In this process a frictionally engaged or positive-fit connection between Kirschner wire 60 and interior wall region 24, or a frictionally engaged or positive-fit connection between Kirschner wire 60 and clamping region 32 can take place. As a result of the design of clamping region 32 with, for example, a cutting edge, by only slight deformation of the outside region of the Kirschner wire 60 it is also possible to bring about a positive-fit connection between the Kirschner wire and clamping region 32, which prevents any relative movement between Kirschner wire 60 and the Kirschner wire clamp.

Furthermore, FIG. 3 shows that the tapering-off fitting region 15 can serve as a centering device in through-hole 51 of bone plate 50 in order to, in this way, be able to reliably fix bone plate 50 to bone 40. It should be noted that with the Kirschner wire clamp according to the invention Kirschner wires of various diameters can be fixed because the design of the clamping mechanism allows a variable diameter of a Kirschner wire 60.

Referring to FIG. 4 there is shown a further embodiment of a Kirschner wire clamp according to the present invention. The embodiment shown in FIG. 4 shows a Kirschner wire clamp in which clamping element 30, guide element 20 and base element 10 are open towards one side so that a Kirschner wire 60 that protrudes beyond a bone 40 and through a through-hole 51 of a bone plate 50 can be laterally inserted into the guide element 20.

For this purpose guide element 20 comprises a lateral opening 28 in the form of a slit that allows lateral insertion of a Kirschner wire. It is sensible if in the fastening region 35 a lateral opening in the clamping element 30 is also provided so that the Kirschner wire can be inserted without hindrance in the lateral slit 28. In the embodiment shown in FIG. 4 base element 10 also comprises a lateral opening 18 in the form of a slit. Corresponding thereto, clamping element 30 comprises recess 38 which also allows lateral insertion of a Kirschner wire.

With the embodiment shown in FIG. 4 it is possible to simply and reliably fix a bone plate to a bone surface by a Kirschner wire fastened to the bone without the free end of the Kirschner wire having to be accessible. Instead, in an installation region that is not much larger than the length of the Kirschner wire clamp, the Kirschner wire clamp shown in FIG. 4 can be fixed to the Kirschner wire in order to fix a bone plate 50 to a surface of a bone 40.

It should be noted that the present invention, apart from the application in the case of Kirschner wires, can also be applied in the case of other, similar, wires and rods, in particular if the wires and rods provide adequate bending stability so that they allow corresponding clamping.

Furthermore, it should be noted that "comprising" does not exclude other elements or process-related steps, and "a" or "an" does not exclude a plural number of elements or steps.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A Kirschner wire clamp comprising:
an axially extending tubular guide member having a first end for contacting a bone plate located on a bone and a second open end, the tubular guide member having a bore with an open slot extending continuously from the first end to the second end open to the bone extending parallel to the axis of the tubular guide member;
a clamp formed as a single piece of material fixedly mounted on the tubular guide member intermediate the first and second ends, the clamp having a first clamp portion attached to an outer surface of the tubular guide and having a section coupled to a deflectable arm including an elongated opening in the arm for receiving a shaft of a Kirschner wire with a longitudinal direction of the elongated opening intersecting a shaft axis of the Kirschner wire, the arm having a relaxed position and a deflected position in which the arm elongate opening applies a force to the Kirschner wire shaft, the elongated opening having an open slot for receiving the shaft of the Kirschner wire by movement of the shaft through the slot in the tubular guide member along a plane containing the axis of the tubular member when the arm is in the deflected position, the first clamp portion fixed in the axial direction to the tubular guide member, the first clamp portion having first gripping ends, the deflectable arm having a second gripping end both extending on one side of the tubular guide member allowing a single-handed operation of the clamp, the tubular element second end located intermediate the first clamping element portion and the clamping element third portion whereby the slot in the elongated opening in the second portion is spaced from the tubular element second end when aligned with the first axis.

2. The Kirschner wire clamp as set forth in claim 1 wherein the first end includes a base element having a tapered outer surface for engaging a hole in the bone plate.

3. A Kirschner wire clamp for clamping a bone plate to a bone comprising:

an axially extending tubular guide member having a first end for contacting a bone plate located on a bone, a second open end and a guide bore extending along a first axis;

a clamp mounted on the tubular guide member intermediate the first and second ends, the clamp having a first clamp portion attached to an outer surface of the tubular guide having a portion coupled to a deflectable arm including an oblong opening in the deflectable arm for receiving a shaft of a Kirschner wire, the deflectable arm having a relaxed position and a deflected position in which the arm opening is capable of applying a force to a Kirschner wire shaft, the first clamp portion fixed in the axial direction to the tubular guide member wherein the deflectable arm has a portion extending beyond the second open end of the tubular guide member, the portion including the oblong opening in the arm and is capable of deflecting to align the oblong opening with the first axis of the guide bore of the tubular guide member wherein the tubular guide member axially extending bore has a wall with a continuous axially extending slot, the axially extending slot in the tubular guide member wall is continuously parallel to the guide bore axis and the oblong opening has a laterally open slot wherein the width of the open slot is smaller than a length of the oblong opening, the slots capable of receiving the shaft of the Kirschner wire by movement of the wire in a single plane when the second portion of the arm is deflected into alignment with the first axis, the tubular element second end located intermediate the first clamping element portion and the clamping element third portion whereby the slot in the elongated opening in the second portion is spaced from the tubular element second end when aligned with the first axis.

4. The Kirschner wire clamp as set forth in claim 3 wherein the deflectable arm is a leaf spring having the slot formed therein for receiving the shaft of the Kirschner wire.

5. A Kirschner wire clamp comprising:
a tubular guide element having first and second ends and bore extending along a first axis for receiving a Kirschner wire, the first end being received by a bone implant;
a clamping element having a first portion fixed to the tubular guide element and extending along a second axis transverse to the first axis of the tubular guide element, the first portion having a gripping region at an end thereof spaced from the tubular element, the clamping element further comprising a second portion connected to the first portion, the second portion extending along a third axis angled with respect to the second axis, the second portion having an elongated opening therein extending along the third axis and a gripping region at an end thereof spaced from the tubular guide element, the second portion being spaced from and deflectable towards the second end of the tubular guide element by action on the gripping regions of the first and second portions, the tubular guide element and the elongated opening having a laterally open slot for receiving a shaft of the Kirschner wire by movement of the shaft along a plane containing the first axis when the second portion is deflected to a position in which the slot in the elongated opening is aligned with the first axis, the tubular element second end located intermediate the first clamping element portion and the clamping element third portion whereby the slot in the elongated opening in the second portion is spaced from the tubular element second end when aligned with the first axis.

6. The Kirschner wire clamp set forth in claim 5 wherein the third axis lies in a plane containing the guide element longitudinal axis.

7. A Kirschner wire clamp comprising:
a tubular guide element having first and second ends and a bore extending continuously along a first axis from the first to second end for receiving a Kirschner wire, the first end being received by a bone implant, the tubular guide element having an open slot communicating with the bore, the slot extending continuously from the first to the second end of the tubular guide element, the slot continuously parallel to the first axis;
a clamping element having a first portion fixed to the tubular guide element and extending along a second axis transverse to the first axis of the tubular guide element the first portion having a gripping region, the clamping element further comprising a second portion connected to the first portion, the second portion extending along a third axis angled with respect to the second axis, and a third portion having a gripping region connected to the second portion and extending away from the first axis towards the gripping region of the first portion, the second portion having an elongated opening therein spaced from and deflectable towards the second end of the tubular guide element, the elongated opening having an open slot for receiving a shaft of the Kirschner wire by movement of the shaft through the slot in the tubular guide element along a plane containing the first axis when the second portion is deflected by a force acting on the third portion gripping region to a position in which the slot in the elongated opening in the second portion is aligned with the first axis, the tubular element second end located intermediate the first clamping element portion and the clamping element third portion whereby the slot in the elongated opening in the second portion is spaced from the tubular element second end when aligned with the first axis.

* * * * *